US012796958B2

(12) United States Patent
Chang

(10) Patent No.: US 12,796,958 B2
(45) Date of Patent: Nov. 17, 2026

(54) BALLISTOCARDIOGRAM DETECTION DEVICE FOR NOISE REDUCTION AND SENSING SYSTEM

(71) Applicant: Humetrics Inc., New Taipei City (TW)

(72) Inventor: Yi-Chung Chang, Taipei City (TW)

(73) Assignee: HUMETRICS INC., New Taipei City (TW)

( * ) Notice: Subject to any disclaimer, the term of this patent is extended or adjusted under 35 U.S.C. 154(b) by 168 days.

(21) Appl. No.: 18/830,828

(22) Filed: Sep. 11, 2024

(65) Prior Publication Data

US 2025/0082228 A1 Mar. 13, 2025

Related U.S. Application Data

(60) Provisional application No. 63/538,077, filed on Sep. 13, 2023.

(51) Int. Cl.
*A61B 5/11* (2006.01)
*A61B 5/00* (2006.01)

(52) U.S. Cl.
CPC .......... *A61B 5/1102* (2013.01); *A61B 5/6892* (2013.01); *A61B 5/7214* (2013.01); *A61B 2562/0219* (2013.01)

(58) Field of Classification Search
CPC .... A61B 2562/0219; A61B 2562/0247; A61B 2562/046; A61B 5/1102; A61B 5/6892; A61B 5/7214
See application file for complete search history.

(56) References Cited

FOREIGN PATENT DOCUMENTS

KR 1020220165509 A 12/2022

*Primary Examiner* — Michael T Rozanski
(74) *Attorney, Agent, or Firm* — Li & Cai Intellectual Property (USA) Office

(57) ABSTRACT

A ballistocardiogram detection device for noise reduction includes a bearing module, a force sensor, a vibration sensor, and a signal processing module. The bearing module is disposed directly or indirectly on a body or back of a test subject. The force sensor and the vibration sensor are disposed on the bearing module. A distance between the vibration sensor and the force sensor is less than 20 cm. The signal processing module is electrically connected to the force sensor and the vibration sensor. The signal processing module is configured to receive signals output from the force sensor and the vibration sensor.

1 Claim, 7 Drawing Sheets

BALLISTOCARDIOGRAM DETECTION DEVICE FOR NOISE REDUCTION AND SENSING SYSTEM

CROSS-REFERENCE TO RELATED PATENT APPLICATION

This application claims the benefit of priority to the U.S. Provisional Patent Application Ser. No. 63/538,077 filed on Sep. 13, 2023 which application is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a ballistocardiogram detection device and a sensing system, and more particularly to a ballistocardiogram detection device for noise reduction and a sensing system.

BACKGROUND OF THE DISCLOSURE

A ballistocardiogram (BCG) is a physiological signal generated by the heart of a living organism. The waveform of the BCG shows the stroke volume output from the heart during each heartbeat, which generates a force impacting the walls of the ascending and descending aorta, causing regular displacements in the body. The BCG effectively reflects the health status of the cardiovascular system. The BCG can be applied in various fields such as heart rate monitoring systems, assessment of cardiac function (systole and diastole), and physiological signal analysis (respiratory rate and blood pressure variations). Additionally, the BCG can be integrated with wearable devices for remote monitoring of heart health in chronic disease patients, and can also be used to analyze cardiac activity during sleep, aiding in the diagnosis of sleep disorders.

Currently, many monitoring devices or instruments that are used by being placed under a mattress for measuring the BCG signal have already been developed. However, since the BCG signal is caused by tiny vibrations of the body of the living organism resulting from heart contraction and relaxation (i.e., the BCG signal itself is a small signal), it is easily affected by interference from other body movements or vibrations of the mattress during detection. Hence, the BCG signals detected by existing monitoring devices have a poor signal-to-noise ratio (SNR). Therefore, how to effectively improve on such devices to overcome the aforementioned problem has become one of the important issues to be addressed in the relevant field.

SUMMARY OF THE DISCLOSURE

In response to the above-referenced technical inadequacy, the present disclosure provides a ballistocardiogram detection device for noise reduction and a sensing system, which can accurately sense the BCG signal of a test subject and achieve a noise reduction effect.

In order to solve the above-mentioned problems, one of the technical aspects adopted by the present disclosure is to provide a ballistocardiogram detection device for noise reduction, which includes a bearing module, a force sensor, a vibration sensor, and a signal processing module. The bearing module is disposed directly or indirectly under a body or on the back of a test subject. The force sensor and the vibration sensor are disposed on the bearing module. A distance between the vibration sensor and the force sensor is less than 20 cm. The signal processing module is electrically connected to the force sensor and the vibration sensor. The signal processing module is configured to receive signals output from the force sensor and the vibration sensor.

In order to solve the above-mentioned problems, another one of the technical aspects adopted by the present disclosure is to provide a ballistocardiogram sensing system, which includes a flexible protective pad, a plurality of detection devices, and a signal processing module. The plurality of detection devices are arranged at a plurality of areas of the flexible protective pad, respectively. Each of the detection devices includes a force sensor and a vibration sensor. Each of the detection devices senses a force that is exerted thereon, as well as a vibration that is generated on the corresponding area of the flexible protective pad, such that the force sensor outputs a force sensing signal, and the vibration sensor outputs a vibration sensing signal. The signal processing module is electrically connected to the force sensor and the vibration sensor in each of the detection devices. The signal processing module is configured to receive the vibration sensing signals from the plurality of vibration sensors and generate a plurality of ballistocardiographic waveforms accordingly, and the signal processing module extracts a plurality of peak points from the plurality of ballistocardiographic waveforms and obtains a plurality of heartbeat intervals from the plurality of peak points.

Therefore, in the ballistocardiogram detection device for noise reduction and the sensing system provided by the present disclosure, by arranging the force sensor and the vibration sensor in close proximity, with a distance of less than 20 cm between them, the vibration sensor and force sensor can be located within the same sensing area. The signal processing module is configured to receive the vibration sensing signals generated by the plurality of vibration sensors and generate a plurality of ballistocardiographic waveforms accordingly, and then obtains a plurality of heartbeat intervals from the plurality of ballistocardiographic waveforms. Further, in response to the force sensing signal generated by the force sensor, the signal processing module filters or applies weights to the plurality of heartbeat intervals, allowing the resulting heartbeat intervals to improve accuracy and signal-to-noise ratio (SNR), thereby achieving noise reduction effects.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
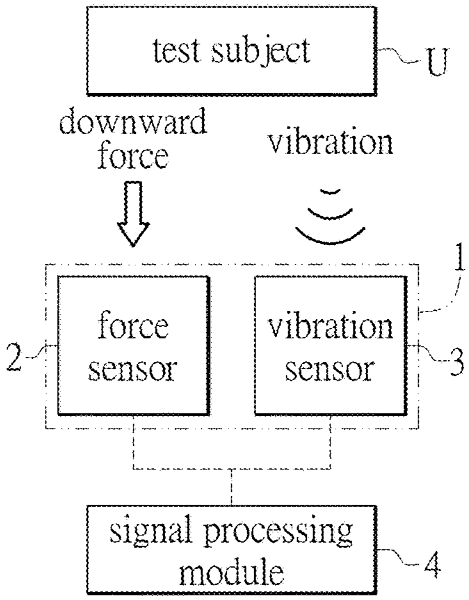
FIG. 1 is a schematic view of a ballistocardiogram detection device according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

Embodiment

Reference is made to FIG. 1. The present disclosure provides a ballistocardiogram (BCG) detection device, which includes a bearing module 1, a force sensor 2, a vibration sensor 3, and a signal processing module 4. The bearing module 1 is disposed directly or indirectly under a body or on the back of a test subject U. The test subject U can be, for example, a human body or that of other animals, but the present disclosure is not limited thereto. In the embodiment of the present disclosure, the test subject U is exemplified by the human body.

The force sensor 2 and the vibration sensor 3 are disposed on the bearing module 1, and the vibration sensor 3 is placed in proximity to the force sensor 2. Preferably, a distance between the vibration sensor 3 and the force sensor 2 is less than 20 cm. Therefore, the vibration sensor 3 and force sensor 2 can be located within a same sensing area. The phases of the signals output by both the vibration sensor 3 and the force sensor 2 can correspond to each other (i.e., the phases of the signals are close to or equal to each other). The signal processing module 4 is electrically connected to the force sensor 2 and the vibration sensor 3. The signal processing module 4 is configured to receive signals output from the force sensor 2 and the vibration sensor 3.

Figure 2:
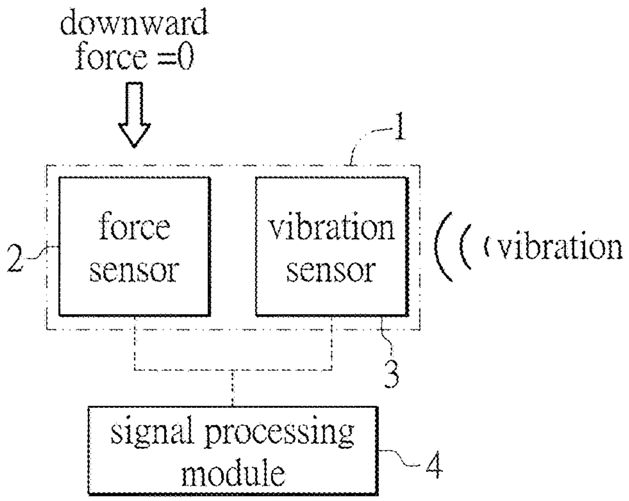
FIG. 2 is another schematic view of the ballistocardiogram detection device according to the present disclosure.

The test subject U (i.e., the human body) can serve as a source of force and vibration. For example, when the bearing module 1 is disposed directly or indirectly on the back of the test subject U, the test subject U exerts a downward force on the bearing module 1, while the force sensor 2 is used to sense the downward force on the bearing module 1 and output a force sensing signal accordingly. The vibration sensor 3 is used to sense a body vibration of the test subject U caused by heartbeats and outputs a vibration sensing signal accordingly. Reference is made to FIG. 2. On the other hand, when the test subject U moves, the back of the test subject U moves away from the sensing area of the force sensor 2 and the vibration sensor 3, and the bearing module 1 is no longer under force (i.e., the downward force is equal to 0), so that the force sensor 2 does not sense any force on the bearing module 1. However, due to the higher sensitivity of the vibration sensor 3 compared to the force sensor 2, the vibration sensor 3 can detect other vibration sensing signals from different sensing areas such as the lower limbs of the test subject U or other nearby objects.

Figure 3:
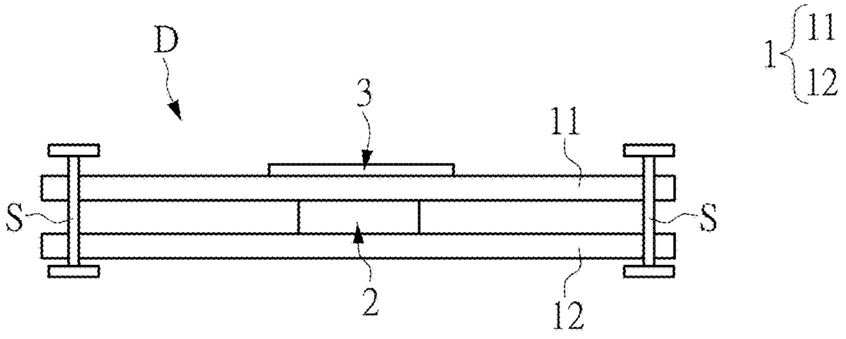
FIG. 3 is a schematic view of a bearing module, a force sensor, and a vibration sensor according to the present disclosure.

Reference is made to FIG. 3. The specific implementation of the BCG detection device is further provided. The BCG detection device includes the bearing module 1, the force sensor 2, and the vibration sensor 3. The bearing module 1 includes a first bearing plate 11 and a second bearing plate 12. The shape and size of the first bearing plate 11 are the same as those of the second bearing plate 12. The first bearing plate 11 is located above the second bearing plate 12. The force sensor 2 is disposed between the first bearing plate 11 and the second bearing plate 12. The vibration sensor 3 is disposed on the first bearing plate 11. Specifically, the vibration sensor 3 is disposed on an upper surface of the first bearing plate 11 and is located directly above the force sensor 2. The bearing module 1 includes two limiting rivets S. The two limiting rivets S are movably fixed on both sides of the bearing plates (i.e., the first bearing plate 11 and the second bearing plate 12). The limiting rivets S restrict the deformation on one side of the first bearing plate 11 within a permissible range, preventing excessive deformation of the first bearing plate 11.

A specific position of the signal processing module 4 is not limited in the present disclosure. The signal processing module 4 can be integrated into the bearing module 1 or serve as an independent component outside of the bearing module 1. The signal processing module 4 can include, but is not limited to, a signal amplifier, a filter, and an analog-to-digital converter, which are used to receive, filter, and convert the detected signals for subsequent analysis and processing.

For example, the force sensor 2 can be a load cell, which includes a resistive strain gauge. When in use, the strain gauge is bonded to a test subject. As the strain gauge stretches or shortens with the test subject, the resistance value of the strain gauge also changes. The deformation of the strain gauge is inferred from the change in the resistance value. Therefore, when the first bearing plate 11 is subjected to a force and deforms, the force sensor 3 detects the deformation caused by the force on the first bearing plate 11 and outputs a force sensing signal accordingly.

For example, the vibration sensor 3 can be a piezoelectric sensor. The piezoelectric sensor can utilize the piezoelectric effect to generate electrical signals when subjected to mechanical stress. In the present disclosure, the vibration sensor 3 is used to detect vibrations generated by the first bearing plate 11 when subjected to a force and to output a vibration sensing signal accordingly.

Figure 4:
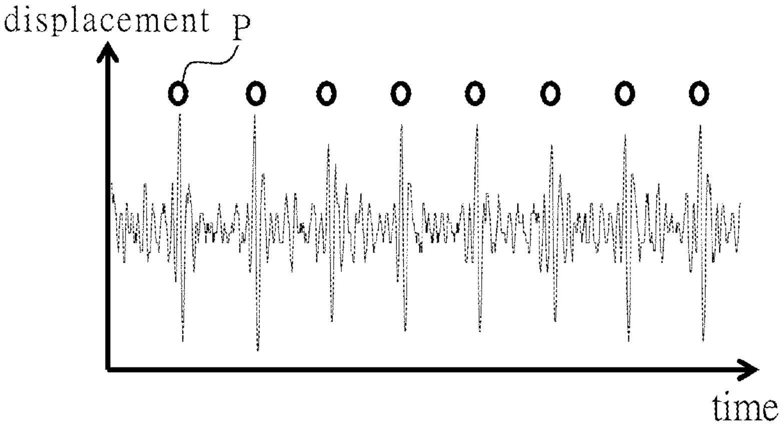
FIG. 4 is a curve diagram showing a vibration waveform obtained by the ballistocardiogram detection device according to the present disclosure.

Reference is made to FIG. 1 and FIG. 4. When the vibration sensor 3 detects body vibrations of the test subject U caused by the heartbeat and outputs a vibration sensing signal accordingly, the signal processing module 4 receives the vibration sensing signal and generate a vibration waveform shown in FIG. 4, that is, a ballistocardiographic (BCG) waveform. The signal processing module extracts a plurality of peak points from the BCG waveform and obtains a plurality of heartbeat intervals P from the plurality of peak points. Similarly, as shown in FIG. 2 and FIG. 5, the vibration sensor 3 also detect vibration sensing signals from other sensing areas (considered as interference signals or noise) and generate another BCG waveform, and the signal processing module 4 extracts a plurality of peak points from the BCG waveform to obtain a plurality of heartbeat intervals Q.

Figure 5:
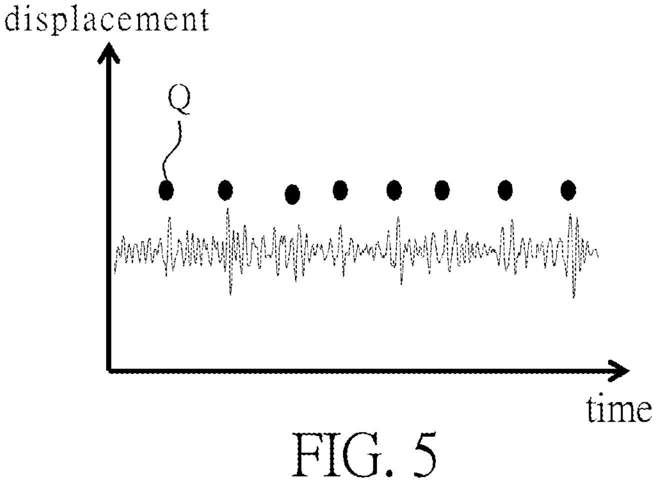
FIG. 5 is a curve diagram showing another vibration waveform obtained by the ballistocardiogram detection device according to the present disclosure.
Figure 6:
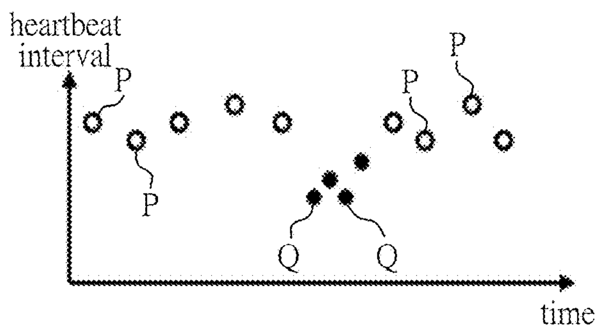
FIG. 6 is a scatter plot diagram showing heartbeat intervals extracted from vibration waveforms according to the present disclosure.
Figure 8:
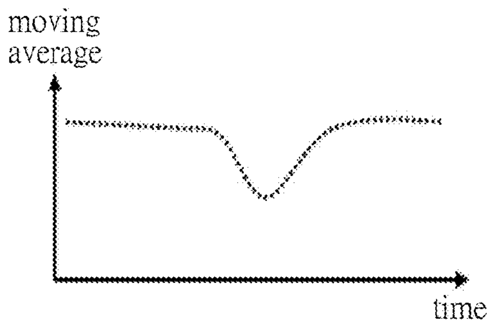
FIG. 8 is a curve diagram showing moving averages obtained from the heartbeat intervals without excluding interference signals according to the present disclosure.

In other words, the vibration sensor 3 detects a composite waveform during the detection process, which includes the waveform generated by vibrations from the sensing area of the vibration sensor 3 (in FIG. 4) as well as the waveform generated by vibrations from other sensing areas (in FIG. 5). Therefore, as shown in FIG. 6, the signal processing module 4 simultaneously extracts a plurality of heartbeat intervals P and Q. Then, as shown in FIG. 8, the signal processing module 4 calculates moving averages for multiple heartbeat interval data P and Q to obtain a moving average curve diagram. In statistics, moving averages are typically used in conjunction with time series to eliminate short-term fluctuations and highlight long-term trends or cycles. Therefore, the BCG waveform diagram (i.e., FIG. 8) obtained through moving average calculations can more accurately reflect the heart rate of the test subject U.

However, as mentioned above, the vibration sensor 3 detects a composite waveform during the detection process. The BCG waveform diagram shown in FIG. 8 does not accurately reflect the heartbeat of the test subject U, as the noise generated by vibrations from other objects is included. Therefore, the signal processing module 4 filters the heartbeat intervals by receiving the force sensing signals from the force sensor 2 and retains the heartbeat intervals P while eliminating the heartbeat intervals Q.

Figure 7:
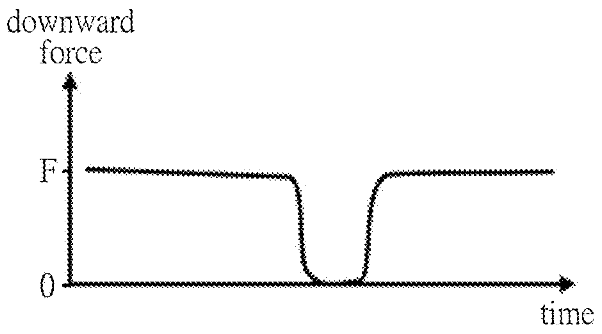
FIG. 7 is a curve diagram showing a downward force obtained by the ballistocardiogram detection device according to the present disclosure.
Figure 9:
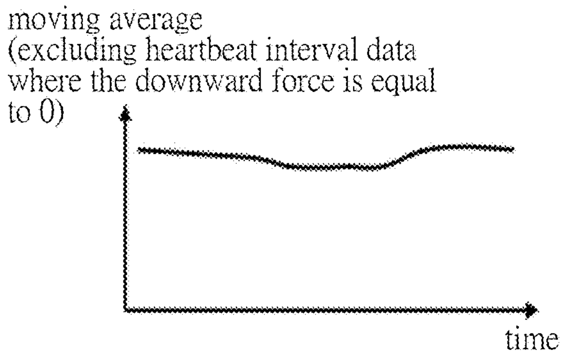
FIG. 9 is a curve diagram showing moving average obtained from the heartbeat intervals after excluding the interference signals according to the present disclosure.

Reference is made to FIG. 6 and FIG. 7. The signal processing module 4 receives the force sensing signals from the force sensor 2 and generates a curve diagram of force versus time (i.e., FIG. 7). Since the force sensor 2 and the vibration sensor 3 are located in the same sensing area, the downward force detected by the force sensor 2 can correspond to the heartbeat intervals. For example, the interval where the force sensor 2 detects a downward force equal to F (F is a predetermined fixed value) corresponds to the distribution of heartbeat intervals P in FIG. 6, and the interval where the force sensor 2 detects a downward force equal to 0 corresponds to the distribution of heartbeat intervals Q in FIG. 6. Therefore, the signal processing module 4 can determine that the heartbeat intervals Q is generated by the noise and eliminate it. In other words, the signal processing module 4 can determine whether the vibrations detected by the vibration sensor 3 are derived from the same sensing area by configuring the force sensor 2 and the vibration sensor 3 to be located in the same sensing area, thereby reducing the error in heart rate calculations. Then, the signal processing module 4 calculates the moving average of the heartbeat intervals based on the heartbeat intervals P that are filtered. As shown in FIG. 9, FIG. 9 represents the BCG waveform diagram obtained after noise reduction and moving average calculations, which can accurately reflect the heart rate of the test subject U.

Figure 10:
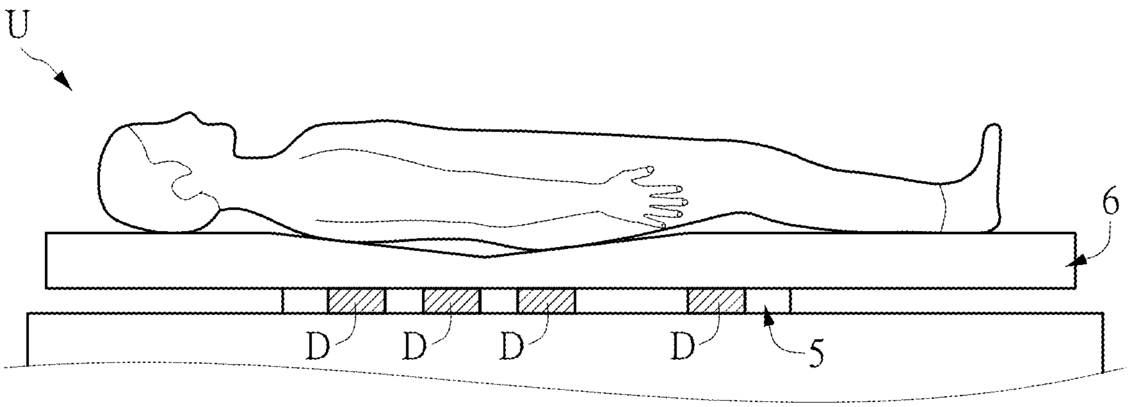
FIG. 10 is schematic side view of a ballistocardiogram sensing system according to the present disclosure.
Figure 11:
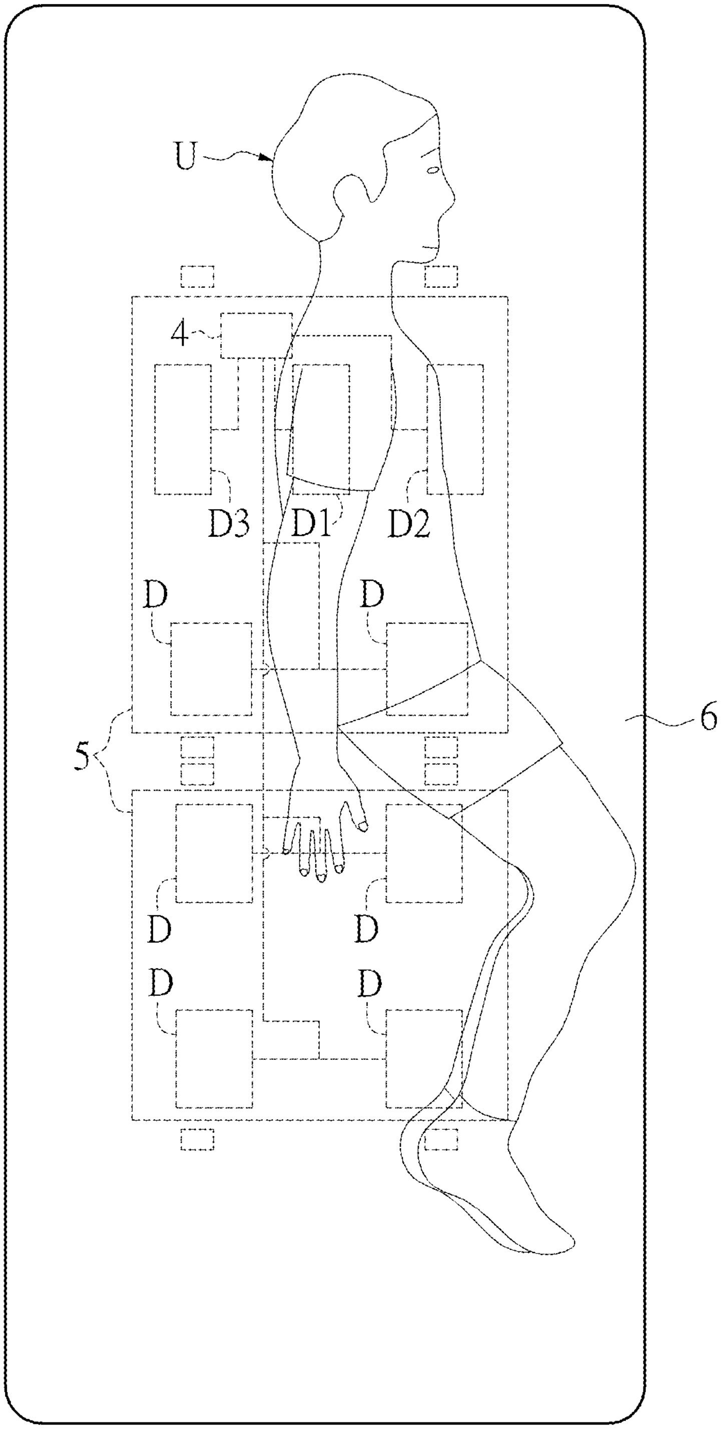
FIG. 11 is schematic top view of the ballistocardiogram sensing system according to the present disclosure.

Reference is made to FIG. 10 and FIG. 11. The present disclosure further provides a ballistocardiogram (BCG) sensing system, which includes a plurality of detection devices D and a flexible protective pad 5. The plurality of detection devices D are arranged at a plurality of areas of the flexible protective pad 5. The flexible protective pad disposed directly or indirectly under a body or on the back of a test subject U. As shown in FIG. 10, for example, the flexible protective pad 5 is disposed under the under a mattress 6, while the user (i.e., the subject U) lies above the mattress 6.

Each of the detection devices D is the BCG detection device mentioned above, which includes the force sensor 2 and the vibration sensor 3 (as shown in FIG. 1). Each of the detection devices D detects a force that is exerted thereon, as well as a vibration that is generated on the corresponding area of the flexible protective pad 5, such that the force sensor 2 outputs a force sensing signal, and the vibration sensor 3 outputs a vibration sensing signal. The signal processing module 4 is electrically connected to the plurality of force sensors 2 and the plurality of vibration sensors 3 in the plurality of detection devices D.

Figure 12:
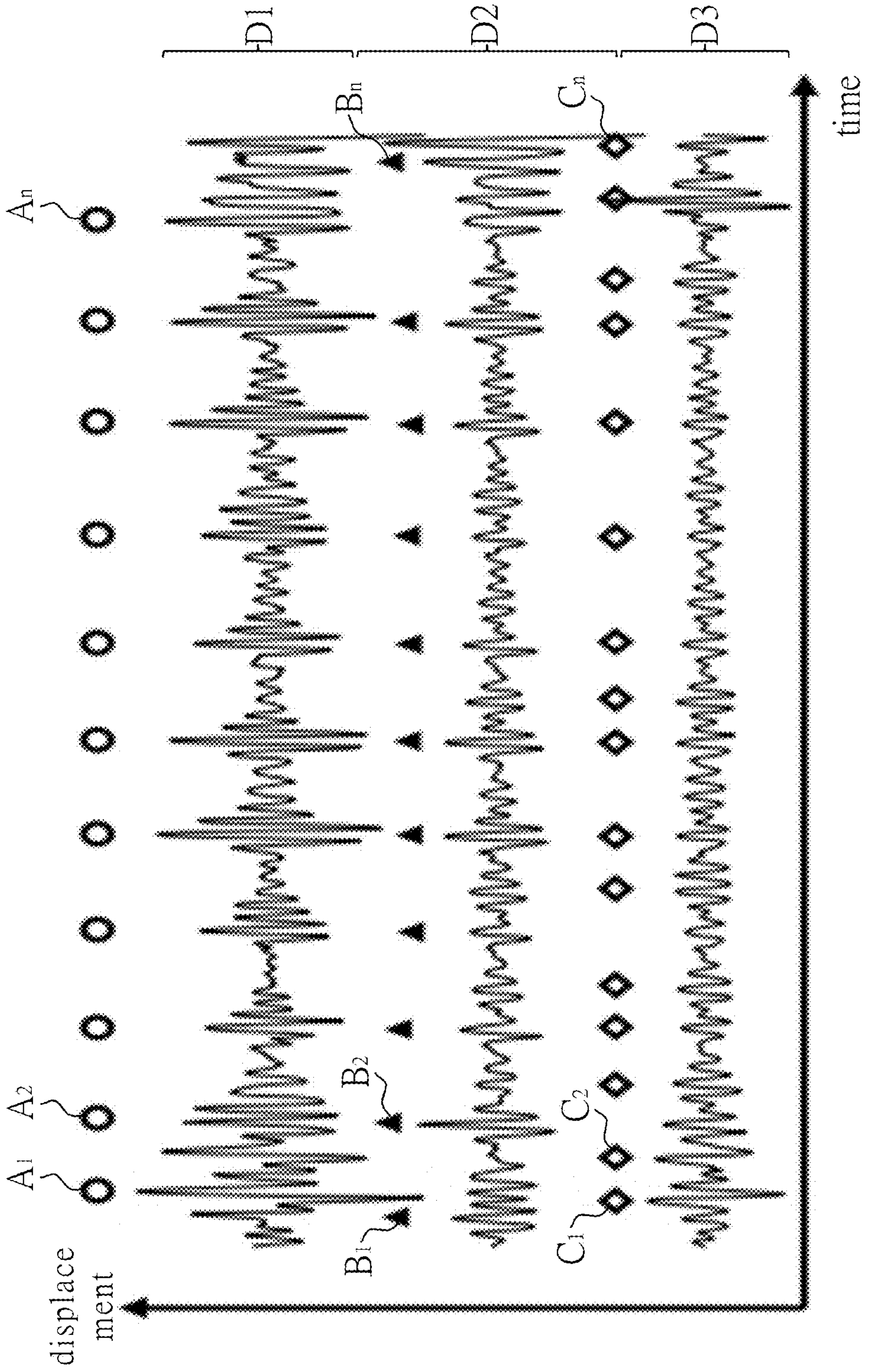
FIG. 12 is a curve diagram showing vibration waveforms obtained by a plurality of ballistocardiogram detection devices in the ballistocardiogram sensing system according to the present disclosure.

Reference is made to FIG. 11. Taking three of the detection devices D in the BCG sensing system as an example, these three detection devices D are further classified into detection devices D1, D2, and D3. As shown in FIG. 11, the user (i.e., the test subject U) is in a side-lying position. From the relative positions of the detection devices D1, D2, and D3 with respect to the user, the detection device D1 is exerted upon by the greatest gravitational force. Therefore, the signals detected by the detection device D1 are more reflective of the user's heart rate compared to those from the detection devices D2 and D3. Reference is made to FIGS. 1, 11, and 12. The signal processing module 4 receives a plurality of vibration sensing signals from vibration sensors 3 in the detection devices D1, D2, and D3, and generates a plurality of BCG waveforms based on the vibration sensing signals. As shown in FIG. 12, the waveform at the top position in FIG. 12 is derived from the detection device D1, the waveform in the middle position is derived from the detection device D2, and the waveform at the bottom position is derived from the detection device D3.

The signal processing module 4 further extracts a plurality of peak points from each of the BCG waveforms and obtains a plurality of heartbeat intervals from the plurality of peak points. As shown in FIG. 12, the heartbeat intervals $A_1$, $A_2$ . . . . $A_n$ are derived from the BCG waveform of the detection device D1, the heartbeat intervals $B_1$, $B_2$ . . . . $B_n$ are derived from the BCG waveform of the detection device D2, and the heartbeat intervals $C_1$, $C_2$ . . . . $C_n$ are derived from the BCG waveform of the detection device D3.

Figure 13:
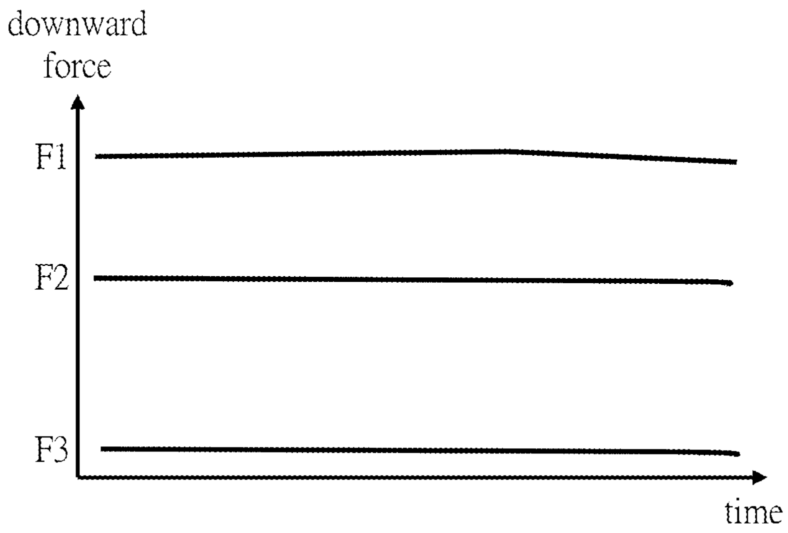
FIG. 13 is a curve diagram showing downward forces obtained by the plurality of ballistocardiogram detection devices in the ballistocardiogram sensing system according to the present disclosure.

Reference is made to FIG. 13. The signal processing module 4 receives the plurality of force sensing signals from the force sensors 2 of the detection devices D1, D2, and D3, and generates multiple curves of force versus time based on these force sensing signals. As shown in FIG. 12 and FIG. 13, the downward force F1 in FIG. 13 corresponds to the BCG waveform of the detection device D1 in FIG. 12, the downward force F2 in FIG. 13 corresponds to the BCG waveform of the detection device D2 in FIG. 12, and the downward force F3 in FIG. 13 corresponds to the BCG waveform of the detection device D3 in FIG. 12.

From the relative positions of the detection devices D1, D2, and D3 with respect to the user shown in FIG. 11, the closer the detection device is to the user, the greater the force exerted on the bearing module 1. Consequently, the vibration waveform obtained by the detection device more accurately reflects the BCG waveform generated by the user's heartbeat. The signal processing module 4 is configured to receive the force sensing signals generated by the plurality of force sensors 2, and assigns a corresponding weight to each of the force sensing signals. The greater the downward force, the larger the assigned weight. For example, as shown in FIG. 13, the weight for downward force F1 is set to $W_1$, the weight for downward force F2 is set to $W_2$, and the weight for downward force F3 is set to $W_3$. The signal processing module 4 performs weighted calculations on the heartbeat intervals based on the weights that are obtained to obtain weighted averages of the heartbeat intervals. As shown in FIGS. 12 and 13, the signal processing module 4 calculates the weighted averages of the heartbeat intervals for the same time period.

For example, in the first time period, the heartbeat intervals $A_1$, $B_1$, and $C_1$ are weighted and averaged to obtain a first weighted average value:

$$((A_1 \times W_1) + (B_1 \times W_2) + (C_1 \times W_3))/(W_1 + W_2 + W_3).$$

In the second time period, the heartbeat interval data $A_2$, $B_2$, and $C_2$ are weighted and averaged to obtain a second weighted average value:

$$((A_2 \times W_1) + (B_2 \times W_2) + (C_2 \times W_3))/(W_1 + W_2 + W_3).$$

In the nth time period, where n is a natural number greater than 3, the heartbeat interval data $A_n$, $B_n$, and $C_n$ are weighted and averaged to obtain a third weighted average value:

$$((A_n \times W_1) + (B_n \times W_2) + (C_n \times W_3))/(W_1 + W_2 + W_3).$$

Through the weighted average calculations, the influence of the vibration sensing signals from the detection device D1, which is closer to the user, is amplified, while the influence of the vibration sensing signals from the detection device D1, which is farther from the user, is reduced. In other words, the farther the detection device D1 is from the user, the weaker the detected vibration sensing signals and the more noise there is. As a result, the BCG waveform diagram obtained after noise reduction and weighted average calculation can accurately reflect the user's heart rate.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A ballistocardiogram sensing system, comprising:

a flexible protective pad disposed directly or indirectly under a body or on a back of a test subject;

a plurality of detection devices arranged at a plurality of areas of the flexible protective pad, respectively, wherein each of the detection devices includes a force sensor and a vibration sensor, each of the detection devices senses a force that is exerted thereon and a vibration that is generated on the corresponding area of the flexible protective pad, such that the force sensor outputs a force sensing signal, and the vibration sensor outputs a vibration sensing signal; and a signal processing module electrically connected to the force sensor and the vibration sensor in each of the detection devices;

wherein the signal processing module is configured to receive the vibration sensing signals from the plurality of vibration sensors and generate a plurality of ballistocardiographic waveforms accordingly, and the signal processing module extracts a plurality of peak points from the plurality of ballistocardiographic waveforms and obtains a plurality of heartbeat intervals from the plurality of peak points;

wherein the signal processing module is configured to receive the force sensing signals generated by the plurality of force sensors, assign a corresponding weight to each of the force sensing signals according to a magnitude of the corresponding force sensed by the corresponding force sensor, and perform weighted calculations on the plurality of heartbeat intervals based on the assigned weights to obtain weighted averages of the plurality of heartbeat intervals.

* * * * *